United States Patent
Halmann et al.

(10) Patent No.: US 10,130,329 B2
(45) Date of Patent: Nov. 20, 2018

(54) DISTINCT NEEDLE DISPLAY IN ULTRASONIC IMAGE

(71) Applicant: General Electric Company, Schenectady, NY (US)

(72) Inventors: Menachem Halmann, Bayside, WI (US); Paul Lawrence Mullen, Waukesha, WI (US); Feng Lin, Niskayuna, NY (US); Eunji Kang, Brookfield, WI (US); Kuiquan Zhang, Wuxi (CN); Bo Li, Wuxi (CN)

(73) Assignee: General Electric Company, Schenectady, NY (US)

( * ) Notice: Subject to any disclaimer, the term of this patent is extended or adjusted under 35 U.S.C. 154(b) by 168 days.

(21) Appl. No.: 14/166,247

(22) Filed: Jan. 28, 2014

(65) Prior Publication Data

US 2015/0209003 A1    Jul. 30, 2015

(51) Int. Cl.
  A61B 5/05     (2006.01)
  A61B 8/08     (2006.01)
  A61B 8/00     (2006.01)
  A61B 34/20    (2016.01)
  A61B 17/34    (2006.01)

(52) U.S. Cl.
  CPC .......... *A61B 8/0841* (2013.01); *A61B 8/4245* (2013.01); *A61B 8/461* (2013.01); *A61B 34/20* (2016.02); *A61B 2017/3413* (2013.01); *A61B 2034/2051* (2016.02)

(58) Field of Classification Search
  USPC ..................................................... 600/424
  See application file for complete search history.

(56) References Cited

U.S. PATENT DOCUMENTS

| | | | |
|---|---|---|---|
| 5,161,536 A * | 11/1992 | Vilkomerson | A61B 8/0833 600/443 |
| 5,329,927 A | 7/1994 | Gardineer et al. | |
| 5,833,627 A | 11/1998 | Shmulewitz et al. | |
| 6,524,247 B2 | 2/2003 | Zhao et al. | |
| 2007/0016035 A1 | 1/2007 | Hashimoto | |
| 2010/0121190 A1* | 5/2010 | Pagoulatos et al. | 600/437 |
| 2010/0298704 A1* | 11/2010 | Pelissier et al. | 600/443 |
| 2011/0137156 A1* | 6/2011 | Razzaque et al. | 600/424 |

(Continued)

FOREIGN PATENT DOCUMENTS

| CN | 201404229 Y | 2/2010 |
|---|---|---|
| JP | 2012-070837 A | 4/2012 |

(Continued)

OTHER PUBLICATIONS

Okazawa et al (Methods for segmenting curved needles in ultrasound images).*

(Continued)

*Primary Examiner* — Joel F Brutus

(57) ABSTRACT

A process for visualization of a needle in an ultrasound image comprises defining a region of an ultrasound image in which a body of a needle is expected using a needle tracking system to predict the location of the needle. The process also includes assigning a probability to a plurality of pixels within the region of the ultrasound image of being representative of the body of the needle, and modifying the display of each pixel having an assigned probability within a predetermined range.

17 Claims, 3 Drawing Sheets

(56) References Cited

U.S. PATENT DOCUMENTS

2012/0078103 A1  3/2012  Tashiro et al.
2012/0209107 A1  8/2012  Guo et al.
2013/0190610 A1  7/2013  Liu

FOREIGN PATENT DOCUMENTS

| JP | 2012-120747 A | 6/2012 |
| WO | 2013033552 A | 3/2013 |
| WO | 2013/111133 A1 | 8/2013 |

OTHER PUBLICATIONS

International Search Report and Written Opinion regarding International Application No. PCT/US2015/013243, dated May 4, 2015, 14 pages.

\* cited by examiner

DISTINCT NEEDLE DISPLAY IN ULTRASONIC IMAGE

BACKGROUND

Ultrasonic imaging is used to examine the interior of living tissue and the image is used to aid in the performance of medical procedures on this tissue. One such procedure is the insertion of a needle to a desired location in the tissue, for instance the insertion of a needle into a lesion or other anomaly in the tissue to take a biopsy. In some cases the full body of the needle and particularly its tip is not readily apparent in the ultrasound image. There are needle-tracking systems that provide an indication of the location of the needle in the tissue. This indication is used as a graphical overlay on an ultrasound image being used to guide the insertion of the needle into the tissue.

SUMMARY

A process for visualization of a needle in an ultrasound image comprises defining a region of an ultrasound image in which a body of a needle is expected using a needle tracking system to predict the location of the needle. The process also includes assigning a probability to a plurality of pixels within the region of the ultrasound image of being representative of the body of the needle, and modifying the display of each pixel having an assigned probability within a predetermined range.

A process for visualization of a needle in an ultrasound guided needle procedure comprises obtaining an ultrasound image that includes the needle inserted in the tissue; selecting a region of the ultrasound image in which the needle is predicted to be located using a non-ultrasound needle tracking system; identifying pixels within the region representative of the needle body as a function of the intensity of each pixel; and assigning a color other than grayscale in the RGB system to each such identified pixel with the depth of the color being a function of the intensity of the pixel.

An apparatus for visualization of a needle in an ultrasound guided needle procedure comprises a needle tracking system that provides a predicted needle body position and an ultrasound imaging system that provides an image of a tissue into which the needle has penetrated. The ultrasound imaging system provides an image of a tissue into which the needle has penetrated and a processing unit. The processing unit receives an ultrasound image which includes the needle in the tissue, selects a region of the image in which the needle body is predicted to be located using the predicted needle body position, identifies a plurality of pixels within the region having an intensity representative of the needle body and modifies the display of each identified pixel.

DETAILED DESCRIPTION

Figure 1:
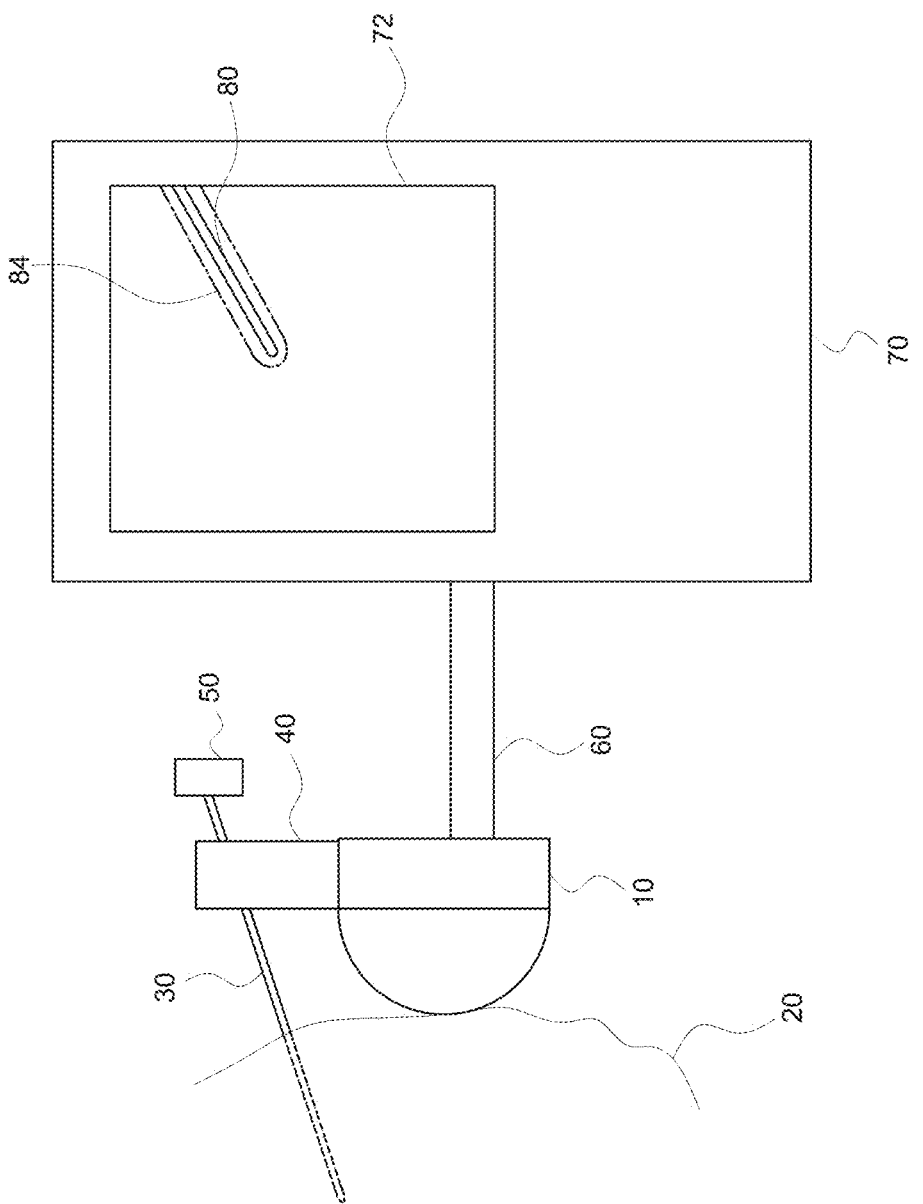
FIG. 1 is a schematic representation of a system for insertion of a needle using ultrasound image and needle tracking guidance.

Referring to FIG. 1, an ultrasound probe head 10 is placed adjacent to living tissue 20, such as human tissue. A needle tracking system 40 is attached to the probe head 10 and measures the depth and angle of insertion of a hollow needle 30. A mechanism 50 for withdrawing a biopsy sample remains attached to the hollow needle 30. However other types of needles 30 used for reasons other than biopsy are contemplated. For example insertion of a needle into a certain portion of the tissue for treatment. The probe head 10 is connected to cables 60 which are, in turn, connected to an ultrasound console 70. The console 70 has a processor for receiving and manipulating signals received from both the probe head 10 and the needle tracking system 40. The console 70 also has a display 72 on which the ultrasound image obtained from the probe head 10 may be viewed. The display may provide a graphical overlay 80 of the hollow needle 30 generated from information provided by the needle tracking system 40.

In one embodiment, the needle tracking system 40 supplies data to the console 70 from which an estimate of the position of the needle 30 is formulated and may be graphically represented a feature 80. In one embodiment, the data from the needle tracking system 40 includes the angle of insertion, the depth of insertion, and the angle of insertion of needle 30 into tissue 20. This data is used to provide a predicted position 80 of needle 30. However, the predicted location 80 of needle 30 may be inaccurate because of limitations of the needle tracking system 40, such as an inability to account for bending of the needle 30 or the variability in measuring the angle of insertion or the depth of insertion. In one embodiment the predicted position 80 of the needle 30 may not be displayed but rather used to assist in identifying the location of the needle from the ultrasound image itself.

In one embodiment needle tracking system 40 may rely upon signals obtained from the needle 30. The needle 30 or a portion thereof may be magnetized and needle tracking system 40 may rely on magnetic interactions with the needle 30. The needle 30 may be provided with a radio frequency identification (RFID) tag and the tag may be probed by the needle tracking system 40. The needle tracking system 40 may rely upon any of the known optical, mechanical, magnetic or electro-magnetic tracking technologies that provides a reasonable estimate of the location of a needle 30 inserted into living tissue 20. In one embodiment the needle tracking system is a non-ultrasound system. In another embodiment the needle tracking system may be an ultrasound system. In one embodiment, the needle tracking system is physically attached to the transceiver of the ultrasound imaging system, and in another embodiment the needle tracking system is within the probe itself. In yet another embodiment the needle tracking system may not be physically attached to the ultrasound probe but in a known relationship to the ultrasound image.

Figure 2:
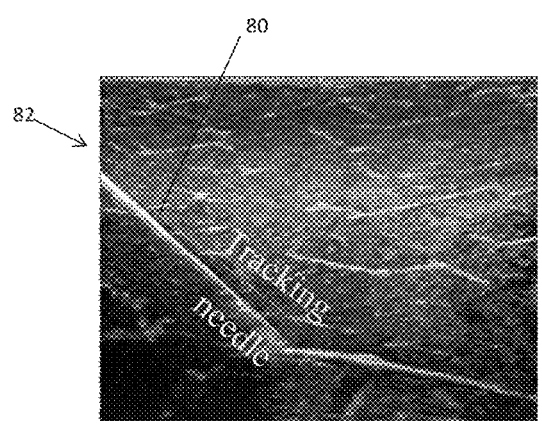
FIG. 2 is an ultrasound image of tissue with an inserted needle and a graphical overlay of a predicted needle position from a needle tracking system.

Referring to FIG. 2, the display 72 provides an ultrasound image 82 of the tissue 20 on which a predicted location 80 of needle 30 has been identified. The predicted location 80 of needle 30 is generated from data supplied by the needle tracking system 40. It provides approximate information as to the location of the needle 30 in the tissue 20. However, the graphical overlay 80 is not obtained from the ultrasound data used to image the tissue 20. Thus it does not represent an ultrasound image of the needle 30.

Figure 3:
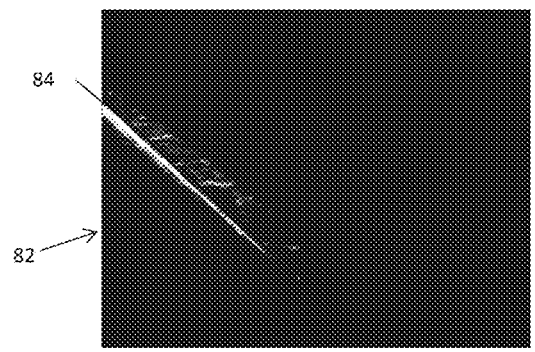
FIG. 3 is an image illustrating a region surrounding a needle tracking system prediction of a needle body.

Referring to FIG. 3, the estimated position 80 of the needle 30 is used to establish a region 84 of ultrasound image 82 that identifies the region in which the needle 30 will be searched in the actual ultrasound image. Alternatively, in one embodiment the region 84 may be illustrated on display 70 by itself or within an outline about the region 84 while still showing entire region 82 on display 70. The predicted location 80 of needle 30 is used to generate a 3D region 84 within which the needle 30 is likely to actually be located. This region 84 can then be searched for ultrasound signal that was generated by the needle 30. This search may involve assigning a probability to each pixel in this 3D region 84 that it is representative of certain aspects of the ultrasound signal obtained from the needle 30. Image processing tools may be used to conduct this search and assign these probabilities. These tools may evaluate the brightness of each pixel, the distance of each pixel from the estimated position 80 of the needle 30 and whether it forms a pattern with other pixels in its vicinity. The distance may be measured as the perpendicular distance from the pixel to the line or path defined by the estimated position 80 of needle 30.

The image processing tools may be used to recognize patterns representative of a thin, bright and elongated object that is oriented similarly to the estimated line, path and/or position 80 of the needle 30. The image processing tools may also take into account the elevation beam width used to create the ultrasound image with pixels falling within a narrower elevation beam width being assigned a different or higher probability than pixels falling within a wider elevation beam. The parameters enumerated above as directing the image processing tools may be utilized individually or in any combination with one or more of the others. The image processing tools may also take into account the distance of a given pixel from a plane that bisects the elevation beam width. In one embodiment the probability or likelihood that the pixel is the needle may at least in part be a function of the elevation thickness of the ultrasound image.

Figure 4:
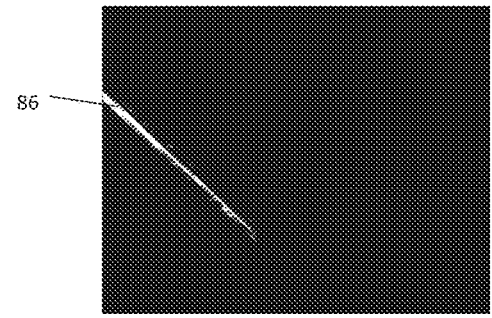
FIG. 4 is an ultrasound image of a needle obtained by applying image-processing tools to the 3D region surrounding a needle tracking system prediction of a needle body.

Referring to FIG. 4, the region of interest 84 may be adjusted to a new region 86 of the ultrasound image to refine the search for needle 30. The adjusted region 86 may be generated by the application of the image processing tools. Region 86 may be larger than or smaller than region 84 or may have a different orientation that region 84. Region 86 is fine-tuned based on the pixels detected as likely to be the needle by image processing tools. Where there is a large enough discrepancy between the actual orientation/location of the needle and the predicted location of the needle, the entire needle may not be present in the initial selected region of interest 84. Hence using the detected needle information, the region of interest 86 is adjusted and the needle is searched again in the new region 86 starting from needle location detected in the previous step. For example if a portion of the pixels of the ultrasound image in region 84 has a high likelihood of being needle 30 a new region 86 may be further searched at the end point of the needle identified in region 84. It may be the case that only a portion of needle 30 is identified in the region 84, while a greater portion of needle 30 may lie outside the initial region 84. Accordingly, a modified region 86 may be searched to increase the change that the entire needle 30 captured in the ultrasound image will be identified.

The creation of region 86 may involve discarding pixels that have less than a threshold probability of being representative of the needle 30. Region 86 may be a virtual construct used simply for computation purposes or may be actually shown on display 70.

Figure 5:
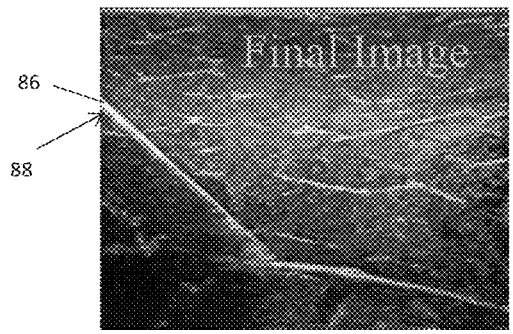
FIG. 5 is an ultrasound image of tissue with an inserted needle with the pixels representative of the needle body given a color other than gray scale.

Referring to FIG. 5, a colorized image 88 of the needle 30 inserted in the tissue 20 may be created by using the probabilities assigned to the pixels found in the 3D region 84 and further limited by region 86. It may be at this point that those pixels with a probability below a certain value are eliminated. In one embodiment, the color assigned to each pixel that has a probability above a threshold is generated using the RGB system. An RGB system is an additive color model in which red, green, and blue colors are added together in various ways to reproduce a broad array of colors. The name of the model comes from the initials of the three additive primary colors, red, green, and blue. However, other types of color models may also be sued. This may involve adjusting the coefficient associated with each of the three colors or channels R, G & B for each pixel in accordance with the probability assigned to that pixel. In one embodiment the adjustments may also reflect the color desired for the colorized ultrasound image 88 of the needle 30. For instance, if the color red were desired the R channel could be given a high intensity while the G and B channels are given a low intensity. In one embodiment a coefficient is created for each pixel that is correlated to the probability assigned to that pixel. Then the quantity (1 minus the coefficient) is multiplied times the strength of two of the channels while the strength of the third channel is left unadjusted. In one embodiment the depth of color of a pixel is a function of its probability in the sense that a pixel with a higher probability will have more of the selected color while that of a lower probability will have a more faded version of the selected color. The color of the pixels in image 88 may have different colors. As a result the colored area may have different colors based on the probability that each area is in fact part of the actual needle 30. In one example the longitudinal feature identified by the pixels may have a first color along one longitudinal edge of the image 88 and may have a second color along a second longitudinal edge of image 88. With pixels intermediate the longitudinal edges having one or more colors between the first color and the second color.

In one embodiment, pixels with a probability greater than a threshold are modified in some way to distinguish them from the other pixels of the ultrasound image of the tissue with the inserted needle. For instance, these pixels may be caused to blink on and off at some convenient frequency or may be assigned a brightness greater than any of the other pixels in the image. In one embodiment the degree of modification of a given pixel is related to the probability assigned to it by the application of the image processing tools. In one embodiment the modification of a given pixel is also related to its distance from a plane that bisects the elevation beam width. In this manner a user may be given an indication if the actual pixels having a high probability of being part of needle 30 are in front of or behind the plane in which the predicted path of the needle lies. In one embodiment a first color may be assigned to pixels in front of the predicted path and a second different color may be assigned to pixels behind the predicted path . . . .

Figure 6:
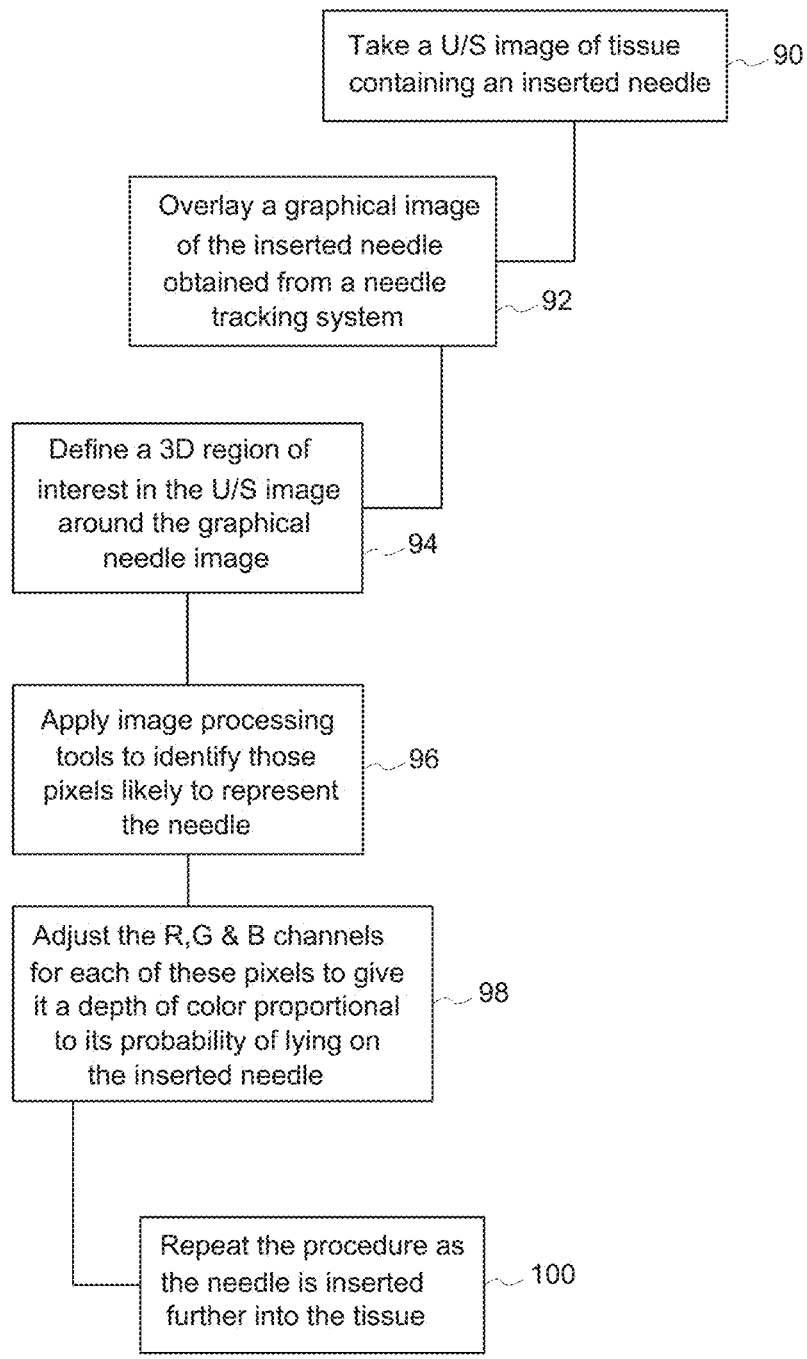
FIG. 6 is a flow chart illustrating a process for dynamically obtaining a colorized image of a needle as the needle is inserted into tissue.

Referring to FIG. 6, a process for creating a colorized image 88 of a needle 30 inserted into tissue 20 is outlined. In one step 90 the process includes obtaining or taking an ultrasound image of tissue containing an inserted needle. In another step 92 a predicted location of the needle within the ultrasound image is determined based on information from a needle tracking system. The information from the needle tracking system includes a predicted location of the needle 30 based on one or more of the entry point of the needle into a patient, the angle of insertion, the depth of insertion and the relationship of the needle tracking system with the ultrasound head. The point of entry may be assigned coordinates with respect to the ultrasound head and/or image. The process also includes in a step 96 identifying a region of interest of the ultrasound image based on the location of the predicted location of the needle from the needle tracking system. The process in a step 96 includes applying image-processing tools to identify those pixels of the ultrasound image likely to represent an ultrasound signal from the inserted needle.

The process in a step 98 includes assigning a color to each of the identified pixels using the three channel RGB system based on the information from the image processing tools. In another embodiment the process step 98 includes modifying the appearance of each of the identified pixels on a display including but not limited to blinking light and or change of shape of each identified pixel. The modification of each pixel may be a function of one or more of the intensity of the pixel, the perpendicular distance of the pixel to the predicted line or path of the predicted needle position, the fit of the pixel with a pattern of other pixels which generally forms a path and or line, and the location of the pixel in the elevation beam. The modification may be a function of at least the fit of a pixel with a pattern of other pixels having an intensity above a given threshold which generally forms a path, where the path may be a predetermined path such as a straight line, or an arcuate path. The step 98 may modify the appearance or color each pixel based on the one or more of the color assigned. In one embodiment, a user interface maybe provided to allow an operator to define the amount of change in color that is assigned to each pixel based on the likelihood of the pixel representing the needle. The interface control would determine the amount of colorization. The interface control could determine the manner in which identified pixels are modified.

The process may be repeated at step 100 to iteratively create a modified and/or colorized image of the needle as it is inserted into the tissue. In this manner the display is dynamic and the color of the pixels are updated as the needle is inserted into the tissue. The process modifies the ultrasound pixels based on the probability that the identified pixel is the needle as a function of one or more of the parameters noted above. It may also be possible to superimpose and display on display 70 the predicted needle position having an appearance different from the appearance of the pixels of the ultrasound image. In further aspect of the invention, the system may receive information as to the type of needle being used including the model and/or gauge. The region of interest may be modified based on the type of needle being used. Further the likelihood of each pixel of the ultrasound image being representative of the needle may also be based in part on the type of needle being used.

The color applied to each pixel identified in the 84 about the predicted location of the needle based on the needle tracking system may be based on a color map. Each pixel is assigned a color that is based on the likelihood of pixel being the needle. In one embodiment each pixel in the ultrasound image is greyscale and the grayscale pixel is modified to a color as discussed herein.

In one example 1 needle recognition software from an ultrasound system obtains the ultrasonic needle image with a transmit beam that is optimized for the needle visualization (i.e. steering angle, frequency, aperture). An electronic tracking system provides a predicted location of the needle. Based on this location, a needle likelihood map is created as a factor of one or more of the insertion point and the tip of the needle identified in terms of the coordinates of the image. A straight line is drawn from the insertion to an end point. Providing a binary image with 1 for those pixels on the line and 0 for the rest. The binary image may be dilated to make the initial line wider. 3. The output of the likelihood and the proximity to the predicted line are multiplied or combined using other "AND" operations. 4. A threshold is applied to the likelihood of each pixel and selecting only those that are above the threshold. Define a desired color to be displayed for each pixel above the threshold. Based on the color decided, a color map is designed, mapping larger intensity to a strong color and smaller intensity to a more gray map color. Intensity below the threshold will have completely gray scale. For instance, if the color red is chosen, intensity of 255 is mapped to (R,G,B)=(255,0,0) while the intensity of 125, which is below the threshold, is mapped to (R,G,B)=(125,125,125). One way to achieve this would be to map the intensity to a coefficient ranging 0 to 1.0. Then, again for the case of red, (1-coefficient) can be multiplied to G and B channel while the R channel value is kept the same (multiplied by 1). In one embodiment the color assigned to certain pixels are a non-gray scale color.

In one embodiment the higher the likelihood that the pixel is the needle the greater the degree of color. If the likelihood is greater than a certain level than a color will be applied to the pixel, while if the likelihood is less than a certain level, the pixel/region will be grayscale.

Although the present disclosure has been described with reference to example embodiments, workers skilled in the art will recognize that changes may be made in form and detail without departing from the spirit and scope of the claimed subject matter. For example, although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described with reference to the example embodiments and set forth in the following claims is manifestly intended to be as broad as possible. For example, unless specifically otherwise noted, the claims reciting a single particular element also encompass a plurality of such particular elements.

What is claimed is:

1. A process for needle visualization comprising:
   inserting a needle configured to be inserted into a tissue;
   obtaining an ultrasound image including the needle, where the ultrasound image is a grayscale image;
   receiving, with a processor, a plurality of signals from a needle tracking system;
   determining, with the processor, an estimated position of the needle in the ultrasound image based on the the plurality of signals from the needle tracking system,
   defining, with the processor, a region comprising a plurality of pixels, where the region is larger than the needle;
   assigning, with the processor, a probability to each of the pixels within the region of the ultrasound image as being representative of the needle;
   creating, with the processor, a colorized image of the needle in the ultrasound image with the processing unit by applying a first color to a first subset of the pixels within the region with a higher probability of being representative of the needle and applying a second color to a second subset of the pixels within the region with a lower probability of being representative of the needle; and displaying the ultrasound image with the colorized image of the needle on a display.

2. The process of claim 1, were the needle tracking system is a non-ultrasound needle tracking system.

3. The process of claim 1, wherein the probability of each of the pixels is a function of an intensity of each of the pixels in the region of the ultrasound image and a perpendicular distance between each of the pixels and the estimated position of the needle obtained from the needle tracking system.

4. The process of claim 1, wherein the probability is a function of a location of each of the pixels within an elevation thickness of the ultrasound image.

5. The process of claim 1, wherein the probability is determined from coordinates of a needle insertion point, an angle of insertion of the needle and a distance of a needle tip from the insertion point by drawing a path between the insertion point and a predicted position of the needle tip.

6. The process of claim 1, wherein the colorized image of the needle is updated as the needle is being inserted.

7. The process of claim 1 wherein the probability is a function of fit of each one of the pixels having an intensity above a predetermined threshold with a pattern of other of the pixels having intensities above the predetermined threshold which forms a path.

8. The process of claim 1 further including adjusting a size of the region and searching for the needle based on a location of the pixels detected as having the higher probability of being representing the needle.

9. A process for needle visualization comprising:
    inserting a needle configured to be inserted into a tissue;
    obtaining an ultrasound image of the tissue containing the needle, where the ultrasound image is a grayscale image;
    receiving, with a processor, a plurality of signals from a needle tracking system;
    determining, with the processor, an estimated position of the needle in the ultrasound image based on the plurality of signals from the needle tracking system;
    defining, with the processor, a region comprising a plurality of pixels, where the region is larger than the needle;
    assigning a probability to each of the pixels within the region of the ultrasound image as being representative of the needle;
    creating, with the processor, a colorized image of the needle by assigning a color other than grayscale in an RGB system to each pixel in the region, where a depth of the color is related to the probability of each one of the pixels representing the needle, where the color is used to modify a first subset of the pixels with a higher probability of being representative of the needle and a more faded version of the color is used to modify a second subset of the pixels with a lower probability of being representative of the needle; and
    displaying the ultrasound image with the colorized image of the needle on a display.

10. The process of claim 9 wherein the probability of each of the pixels is also a function of its fit with a pattern of the other pixels having an intensity above a given threshold which forms a path.

11. The process of claim 10 wherein the needle tracking system is used to create a prediction of a location of the needle and the color of each pixel is also a function of its distance to a predicted location of the needle.

12. The process of claim 11 wherein a coefficient is created for each pixel as a function of an intensity of an identified pixel, and is applied to a channel of the RGB system.

13. The process of claim 12 wherein a prediction of the location of the needle is created by forming a path between a point of insertion of the needle and a predicted location of its tip obtained using a distance of insertion and an angle of insertion provided by the needle tracking system.

14. An apparatus for needle visualization in an ultrasound guided needle procedure comprising:
    a needle tracking system;
    an ultrasound imaging system that provides an image including a needle;
    a display; and
    a processor, wherein the processor is configured to:
        receive an ultrasound image including the needle, where the ultrasound image is a grayscale image;
        determine an estimated position of the needle in the ultrasound image based on a plurality of signals from the needle tracking system;
        define a region comprising a plurality of pixels, where the region is larger than the needle;
        assign a probability to each of the pixels in the region as being representative of the needle;
        create a colorized image of the needle in the ultrasound image by applying a first color to a first subset of the pixels within the region with a higher probability of being representative of the needle and applying a second color to a second subset of the pixels within the region with a lower probability of being representative of the needle; and
        display the ultrasound image with the colorized image of the needle on the display.

15. The apparatus of claim 14 wherein the needle tracking system is a non-ultrasound needle tracking system and the estimated position of the needle is determined from a point of entry of the needle, an angle of entry of the needle and a distance of penetration of the needle from the point of entry.

16. The apparatus of claim 14 wherein the needle tracking system provides the estimated position of the needle from a signal obtained from the needle.

17. The apparatus of claim 14 further including a user interface control to define a change of appearance of each of the plurality of pixel.

* * * * *